United States Patent [19]
Yaver et al.

[11] Patent Number: 5,594,119
[45] Date of Patent: Jan. 14, 1997

[54] GENE ENCODING CARBOXYPEPTIDASE OF *ASPERGILLUS NIGER*

[75] Inventors: Debbie S. Yaver; Sheryl A. Thompson, both of Davis, Calif.

[73] Assignee: Novo Nordisk A/S, Bagsvaerd, Denmark

[21] Appl. No.: 309,341

[22] Filed: Sep. 20, 1994

[51] Int. Cl.$^6$ .................................................. C07H 21/04
[52] U.S. Cl. .................................................. 536/23.2
[58] Field of Search ..................... 435/69.1, 172.3, 435/254.3, 320.1; 536/23.2, 23.74

[56] References Cited

FOREIGN PATENT DOCUMENTS

WO92/17595 10/1992 WIPO.

OTHER PUBLICATIONS

Dal Degan et al. (1992) App. Env. Microbiol. 58:2144–2152.
Krishnan et al. (1986) J. Chrom. 370:315–326.
de Ruiter–Jacobs et al. (1989) Curr. Genet. 16:159–163.
L. Valls et al., Cell, vol. 48, pp. 887–897 (1987).
Berka et al., Gene, vol. 86, No. 2, pp. 153–162 (1990).
Yaver et al., 34th Annual Meeting of ASCB, Molecular Biol. Cell, 5 (Suppl.) ISSN: 1059–1525 (1994).
Sørensen et al., Carlsberg Res. Commun., vol. 54, pp. 193–202 (1989).
Jarai et al., Gene, vol. 145, pp. 171–178 (1994).
Frederick et al., Gene, vol. 125, pp. 57–64 (1993).
Svendsen et al., FEBS Letters, vol. 333, No. 1,2, pp. 39–43 (1993).
Woolford et al., Molecular & Cellular Biology, vol. 6, No. 7, pp. 2500–2510 (1986).
Mukhtar et al., Gene, vol. 121, pp. 173–177 (1992).
Ammerer et al., Molecular & Cellular Biology, vol. 6, No. 7, pp. 2490–2499 (1986).
Stevens et al., J. of Cell Biology, vol. 102, pp. 1551–1557 (1986).
Rodney Rothstein, Methods in Enzymology, vol. 194, pp. 281–301 (1991).

*Primary Examiner*—Robert A. Wax
*Assistant Examiner*—Lisa J. Hobbs
*Attorney, Agent, or Firm*—Steve T. Zelson, Esq.; Elias J. Lambiris, Esq.

[57] ABSTRACT

The present invention relates to a gene encoding an ascomycete or deuteromycete carboxypeptidase Y gene, and host cells modified so as to produce reduced amounts of carboxypeptidase.

9 Claims, 13 Drawing Sheets

FIG. 1
(1 OF 6)

```
                TCCTCTGCCT ACTCATCCCA TCACCATCTC AATTCATACC GCCCCCGTGG GGTTTCAGCA CCA
                    10         20         30         40         50         60

69          78          87          96         105         114
>
ATG AGA GTC CTT CCA GCT GCT ATG CTG GTT GGA GCG GCC ACG GCG GCC GTT CCT
MET Arg Val Leu Pro Ala Ala MET Leu Val Gly Ala Ala Thr Ala Ala Val Pro 123         132         141         150         159         168
CCC TTC CAG CAG CAG GTC CTT GGA AAC GGT GCC AAG CAC GGT GCC GAC CAT GCG
Pro Phe Gln Gln Gln Val Leu Gly Asn Gly Ala Lys His Gly Ala Asp His Ala 177         186         195         204         213         222
GCC GAG GTC CCT GCG GAT CAC AGT GCC GAC GGG TTC TCC AAG CCG CTG CAC GCA
Ala Glu Val Pro Ala Asp His Ser Ala Asp Gly Phe Ser Lys Pro Leu His Ala 231         240         249         258         267         276
TTC CAG GAG GAG CTG AAG TCT CTC GAC TCT GAC GAG GCT CGT AAG CTT TGG GAT GAG
Phe Gln Glu Glu Leu Lys Ser Leu Ser Asp Glu Ala Arg Lys Leu Trp Asp Glu 285         294         303         312         321         330
GTG GCC AGC TTC TTC CCG GAG AGC ATG GAT CAG AAC CCT CTC TTT TCC CTC CCC
Val Ala Ser Phe Phe Pro Glu Ser MET Asp Gln Asn Pro Leu Phe Ser Leu Pro
```

FIG. 1
(2 OF 6)

```
      339       348       357       366       375       384
      |AAG AAC |CAC AAC |CGC CGT |CCC GAC |TCG CAC |GAC CAC |ATC GTC |CGC GGC |TCC
       Lys Lys His Asn Arg Arg Pro Asp Ser His Asp His Ile Val Arg Gly Ser
      393       402       411       420       429       438
      |GAC GTT |CAG AGC |GTC TGG |GTC ACT |GGT GAG |AAC GGT |GAG AAG |GAG CGC |GAG GTC
       Asp Val Gln Ser Val Trp Val Thr Gly Glu Asn Gly Glu Lys Glu Arg Glu Val
      447       456       465       474       483       492
      |GAT GGC |AAG CTG |GAA GCC |TAT GAT |CTC AGG |GTC AAG |AAG ACC |GAT CCT |GGC TCT
       Asp Gly Lys Leu Glu Ala Tyr Asp Leu Arg Val Lys Lys Thr Asp Pro Gly Ser
      501       510       519       528       537       546
      |CTT GGC |ATC GAC |CCC GGG |GTG AAG |CAG TAC |ACC GGT |TAT CTC |GAT GAC |AAC GAG
       Leu Gly Ile Asp Pro Gly Val Lys Gln Tyr Thr Gly Tyr Leu Asp Asp Asn Glu
      555       564               581       591       601       611
      |AAT GAT |AAG CAT |TTG TTC |TAC T     GTAAGCACAC CTTGGTTCAA GATCACGCTT TTTATATGCT
       Asn Asp Lys His Leu Phe Tyr Trp
      621       631       641       650       659       668
      CTGGATATCT AACGCAACTT AG GG |TTC GAG |TCT CGC |AAT GAC |CCC GAG |AAT GAT
                                   Phe Phe Glu Ser Arg Asn Asp Pro Glu Asn Asp
```

FIG. 1
(3 OF 6)

```
                677           686           695           704           713           722
         |   |   |   |   |   |   |   |   |   |   |   |   |   |   |   |   |   |
         CCC GTT CTG TGG AAC GGT CCT GGG TGC TCT TCC CTC ACC GGT CTC
         Pro Val Leu Trp Asn Gly Pro Gly Cys Ser Ser Leu Thr Gly Leu 731           740           749           758           767           776
         |   |   |   |   |   |   |   |   |   |   |   |   |   |   |   |   |   |
         TTC ATG GAG CTT GGC CCT AGC AGC AAG ATC CAG CCG GTC TAC AAT
         Phe MET Glu Leu Gly Pro Ser Ser Lys Ile Gln Pro Val Tyr Asn 785           794           803           812           821           830
         |   |   |   |   |   |   |   |   |   |   |   |   |   |   |   |   |   |
         GAC TAC GCT TGG AAC TCC AAC GCG TCC GTG ATC TTC CTT GAC CAG CCT GTC AAT
         Asp Tyr Ala Trp Asn Ser Asn Ala Ser Val Ile Phe Leu Asp Gln Pro Val Asn 839           848           857           866           875           884
         |   |   |   |   |   |   |   |   |   |   |   |   |   |   |   |   |   |
         GTC GGT TAC TCC TAC AGT AAC TCT GCT GTC AGC GAC ACG GTC GCT GGC AAG
         Val Gly Tyr Ser Tyr Ser Asn Ser Ala Val Ser Asp Thr Val Ala Gly Lys 893           902           911           920           929           938
         |   |   |   |   |   |   |   |   |   |   |   |   |   |   |   |   |   |
         GTC TAT GCC TTG CTT ACC CTC TTC TTC AAA CAA TTC CCC GAG TAT GCT
         Val Tyr Ala Leu Leu Thr Leu Phe Phe Lys Gln Phe Pro Glu Tyr Ala 947           956           965           974           983           992
         |   |   |   |   |   |   |   |   |   |   |   |   |   |   |   |   |   |
         GAC GTC CAC ATT GCC GGT GAA TCT TAT GCT GGT CAC TAT ATC CCC GTC TTC
         Asp Val His Ile Ala Gly Glu Ser Tyr Ala Gly His Tyr Ile Pro Val Phe

GCA GAC TTC CAC
                Gln Asp Phe His
```

FIG. 1
(4 OF 6)

```
       1001            1010            1019            1028            1037            1046
        |GCT TCG GAG ATC CTG TCT CAC AAG AAG CGC AAC ATC AAC CTG CAG TCC GTT CTC
         Ala Ser Glu Ile Leu Ser His Lys Lys Arg Asn Ile Asn Leu Gln Ser Val Leu 1055            1064            1073            1082            1091            1100
        |ATT GGC AAC GGT CTC ACC GAC GGA TAC ACC CAG TAC GAG TAC CGT CCC ATG
         Ile Gly Asn Gly Leu Thr Asp Gly Tyr Thr Gln Tyr Glu Tyr Arg Pro MET 1109            1118            1127            1136            1145            1154
        |GCC TGC GGT GAC GGC GGT TAC CCA GCT GTC TTG GAC GAG AGC TCC TGC CAG TCC
         Ala Cys Gly Asp Gly Gly Tyr Pro Ala Val Leu Asp Glu Ser Ser Cys Gln Ser 1163            1172            1181            1190            1199            1208
        |ATG GAC AAC GCT CTT CCT CGC TGC CAG TCT ATG ATT GAG TCT TGC TAC AGT TCC
         MET Asp Asn Ala Leu Pro Arg Cys Gln Ser MET Ile Glu Ser Cys Tyr Ser Ser 1217            1226            1235            1244            1253            1262
        |GAG AGC GCT TGG GTT TGT GTC CCG GCC TCC ATC TAC TGT AAC AAC GCC CTC CTT
         Glu Ser Ala Trp Val Cys Val Pro Ala Ser Ile Tyr Cys Asn Asn Ala Leu Leu 1271            1280            1289            1298            1307            1316
        |GCC CCT TAC CAG CGC ACT GGG CAG AAC GTC TAT GAT GTC CGT GGT AAG TGC GAG
         Ala Pro Tyr Gln Arg Thr Gly Gln Asn Val Tyr Asp Val Arg Gly Lys Cys Glu
```

FIG. 1
(5 OF 6)

```
                 1325            1334            1343            1352            1361            1370
                  |               |               |               |               |               |
        GAT     AGC     TCT     AAC     CTT     TGC     TAC     TCG     GCT     ATG     GGC     TAC     GTC     AGC     GAC     TAC     CTG     AAC
        Asp     Ser     Ser     Asn     Leu     Cys     Tyr     Ser     Ala     MET     Gly     Tyr     Val     Ser     Asp     Tyr     Leu     Asn 1379            1388            1397            1406            1415            1424
                  |               |               |               |               |               |
        AAG     CCC     GAA     GTC     ATC     GAG     GCT     GTT     GGC     GCT     GAG     GTC     AAC     GGC     TAC     GAC     TCG     TGC
        Lys     Pro     Glu     Val     Ile     Glu     Ala     Val     Gly     Ala     Glu     Val     Asn     Gly     Tyr     Asp     Ser     Cys 1433            1442            1451            1460            1469            1478
                  |               |               |               |               |               |
        AAC     TTT     GAC     ATC     AAC     CGC     AAC     TTC     CTC     TTC     CAC     GGT     GAC     TGG     ATG     AAG     CCC     TAC
        Asn     Phe     Asp     Ile     Asn     Arg     Asn     Phe     Leu     Phe     His     Gly     Asp     Trp     MET     Lys     Pro     Tyr 1487            1496            1505            1514            1523            1532
                  |               |               |               |               |               |
        CAC     CGC     CTC     GTT     CCG     GGA     CTC     CTG     GAG     CAG     ATC     CCT     GTC     TTG     ATC     TAT     GCC     GGT
        His     Arg     Leu     Val     Pro     Gly     Leu     Leu     Glu     Gln     Ile     Pro     Val     Leu     Ile     Tyr     Ala     Gly 1541            1550            1559            1568            1577            1586
                  |               |               |               |               |               |
        GAT     GCT     GAT     TTC     ATT     TGC     AAC     TGG     CTG     GGC     AAC     AAG     GCC     TGG     ACT     GAA     GCC     CTG
        Asp     Ala     Asp     Phe     Ile     Cys     Asn     Trp     Leu     Gly     Asn     Lys     Ala     Trp     Thr     Glu     Ala     Leu 1595            1604            1613            1622            1631            1640
                  |               |               |               |               |               |
        GAG     TGG     CCC     GGA     CAG     GCT     GAA     TAT     GCC     TCC     GCT     GAG     CTG     GAT     CTG     GTC     ATT
        Glu     Trp     Pro     Gly     Gln     Ala     Glu     Tyr     Ala     Ser     Ala     Glu     Leu     Asp     Leu     Val     Ile
```

FIG. 1
(6 OF 6)

```
      1649        1658         1667         1676         1685         1694
     GTC GAC AAT GAG CAC ACG GGC AAG AAG ATT GGC CAG GTT AAG TCC CAT GGC AAC
     Val Asp Asn Glu His Thr Gly Lys Lys Ile Gly Gln Val Lys Ser His Gly Asn
      1703        1712         1721         1730         1739         1748
     TTC ACC TTC ATG CGT CTC TAT GGT GGC CAC ATG GTC CCG ATG GAC CAG CCC
     Phe Thr Phe MET Arg Leu Tyr Gly Gly His MET Val Pro MET Asp Gln Pro
      1757        1766         1775         1784         1793        1809
                                                                  ⎯⎯⎯>
     GAG TCG AGT CTC GAG TTC TTC AAC CGC TGG TTG GGA GGT GAA TGG TTC TAA AGACGTGCTA
     Glu Ser Ser Leu Glu Phe Phe Asn Arg Trp Leu Gly Gly Glu Trp Phe
      1819        1829         1839         1849         1859         1869        1879
     CCACCGCATA TAGACTTTCT GGTCATTTCG GTGACACTGC AGATATGTTT CTTAACGATA GTTTGAGCAT
      1889        1899         1909         1919         1929         1939        1949
     GCTTGTCAAT GCCCACTAGT CCCGATCCTT ATATGTTGCA TGGTATCTAT GAGTTTGTC ACTATAGTGC
      1959        1969         1979         1989         1999         2009        2019
     ATTATACAATG TGTACTTCGT ATGAGAATGA ATCGATCGCA TTTACACGCA TATAAATAGT ACCCACCTCC
      2029        2039         2049         2059         2068
     GCCTGGACAT GAATTAGGCC CGGCCAGTCG TTTACATACA GTGCTAGAA
```

FIG. 2
(1 OF 6)

```
         10         20         30         40         50         60         70
GCGGCCGCTG CTACTTGCTT TTTCTAATTT GATACTTTTG TGTCCGTACC GTACCTTCCA GACCGCAAGG 80         90        100        110        120        130    139

TACCCATCCT CTACCTACTC ATCCCATCAT CATCTCGATT TCATACCAAC CCCGTTGGGT TTCAACACA
```

```
                                                        start of propeptide
                                                             1 ↓
                                                                193
   148      157      166      175           229      238      247
>  |        |        |        |        |    |        |        |
ATG AGA GTT CTT CCA GCT GCT ATG CTG GTT GGA GCG GGC ACT GCG GCC GTC CCT
MET Arg Val Leu Pro Ala Ala MET Leu Val Gly Ala Gly Thr Ala Val Pro 202      211      220           265      274      283      292      301
   |        |        |        |        |        |        |        |        |
CCC TTC CAG CAG GTC CTT GGA GGT AAC GGT GCC AAG CAC GGT GAT CAC AGT GCC GAC CAT GCG
Pro Phe Gln Gln Val Leu Gly Gly Asn Gly Ala Lys His Gly Asp His Ser Ala Asp His Ala 256              274              292              310              328              346              355
   |        |        |        |        |        |        |        |        |        |
GCC GAG GTC CCT GCG GAT CAC AGT GCC GAC GGG CCG CTG CAC GCA CTC TGG GAT GAG
Ala Glu Val Pro Ala Asp His Ser Ala Asp Gly Pro Leu His Ala Leu Trp Asp Glu 355
   |        |        |        |        |        |        |        |
TTC CAG GAG GAG CTG AAG TCT CTC GAT GAG GCT CGT AAG CTC TGG GAT GAG
Phe Gln Glu Glu Leu Lys Ser Leu Ser Asp Glu Ala Arg Lys Leu Trp Asp Glu
```

FIG. 2
(2 OF 6)

```
     364        373        382        391        400        409
 |GTT|AGC|TTC|TTC|CCG|GAG|AGC|ATG|GAT|CAG|AAC|CCT|CTC|TTC|TCC|CTC|CCC
  Val Ala Ser Phe Phe Pro Glu Ser MET Asp Gln Asn Pro Leu Phe Ser Leu Pro 418        427        436        445        454        463
 |AAG|AAG|CAC|AAC|CGC|CCC|GAC|CAC|CAC|TGG|GAC|CAC|ATC|GTC|CGC|GGC|TCC
  Lys Lys His Asn Arg Arg Pro Asp His His Trp Asp His Ile Val Arg Gly Ser 472        481        490        499        508        517
 |GAC|GTT|CAG|AGC|GTC|ACT|GGT|GTT|GAG|AAC|GGT|GAG|AAG|GAG|CGT|GAG|GTC
  Asp Val Gln Ser Val Trp Val Thr Gly Glu Asn Gly Glu Lys Glu Arg Glu Val
                                                  predicted N-terminus of mature CPY
     526        535        544        ↓ 553     562        571
 |GAT|GGC|AAG|CTG|GAA|TAT|GAT|AGG|GTC|AAG|AAG|ACC|GAT|CCT|AGC|TCT
  Asp Gly Lys Leu Glu Ala Tyr Asp Arg Val Lys Lys Thr Asp Pro Ser Ser 580        589        598        607        616        625
 |GAC|ATC|GAC|CCT|GGC|GTA|AAG|CAG|TAC|ACC|GGT|TAT|CTC|GAC|AAC|GAG
  Asp Ile Asp Pro Gly Val Lys Gln Tyr Thr Gly Tyr Leu Asp Asn Glu

|CTT|GGC|ATC|GAC|CCT|GGC|GTA|AAG|CAG|TAC|ACC|GGT|TAT|CTC|GAC|AAC|GAG
  Leu Gly Ile Asp Pro Gly Val Lys Gln Tyr Thr Gly Tyr Leu Asp Asn Glu
```

FIG. 2 (3 OF 6)

```
      634         643         652         661         670         679
AAC GAC|AAG CAT CTG|TAC TGG TTC|TTC GAG TCT|CGC AAT GAC|CCC GAG AAT
Asn Asp Lys His Leu Tyr Trp Phe Phe Glu Ser Arg Asn Asp Pro Glu Asn 688         697         706         715         724         733
GAC CCT|GTT GTG CTG|CTG TGG AAC|CTG GGT CCT|GGA TGC TCC|TCC CTC ACC
Asp Pro Val Val Leu Leu Trp Asn Leu Gly Pro Gly Cys Ser Ser Leu Thr 742         751         760         769         778         787
CTT TTC|ATG GAG CTC|GGC CCT AGC|AGC ATC AAC|AAG ATC CAG|CCG GTC TAC
Leu Phe MET Glu Leu Gly Pro Ser Ser Ile Asn Lys Ile Gln Pro Val Tyr 796         805         814         823         832         841
AAC GAC|TAC GCT TGG|AAC TCC AAC|GCG TCC GTG|ATC TTC CTT|GAC CAG CCT GTC
Asn Asp Tyr Ala Trp Asn Ser Asn Ala Ser Val Ile Phe Leu Asp Gln Pro Val 850         859         868         877         886         895
AAC GAC|TAC TCT TAC|AGC AAC TCT|GCT GTC AGC|GAC ACC CTT|GTT GCT GCT GGC
Asn Asp Tyr Ser Tyr Ser Asn Ser Ala Val Ser Asp Thr Leu Val Ala Ala Gly 904         913         922         931         940         949
AAG GAC|GTC TAT GCC|CTT CTT CTG|ACC CTC TTC|TTT AAA CAA|CCC GAG TAT GCC
Lys Asp Val Tyr Ala Leu Leu Leu Thr Leu Phe Phe Lys Gln Pro Glu Tyr Ala
```

FIG. 2
(4 OF 6)

```
      958         967         976         985         994        1003
      |           |           |           |           |           |
  AAG CAG GAC TTC CAC GGT TCC GAA TAT GCT GGT CAC TAT ATC CCC GTC
  Lys Gln Asp Phe His Gly Ser Glu Tyr Ala Gly His Tyr Ile Pro Val 1012        1021        1030        1039        1048        1057
      |           |           |           |           |           |
  TTT GCT TCG GAG ATT TTG TCT CAC AAG AAG CGC AAC ATC AAC CTG CAG TCC GTT
  Phe Ala Ser Glu Ile Leu Ser His Lys Lys Arg Asn Ile Asn Leu Gln Ser Val 1066        1075        1084        1093        1102        1111
      |           |           |           |           |           |
  CTT ATT GGC AAC GGT CTC ACC GAC GGT CTC ACT CAG TAC GAG TAC CGT CCC
  Leu Ile Gly Asn Gly Leu Thr Asp Gly Leu Thr Gln Tyr Glu Tyr Arg Pro 1120        1129        1138        1147        1156        1165
      |           |           |           |           |           |
  ATG GCC TGT GGT GAC GGT GGT TAC CCA GCT GTC TTG GAC GAG GGC TCC TGC CAG
  MET Ala Cys Gly Asp Gly Gly Tyr Pro Ala Val Leu Asp Glu Gly Ser Cys Gln 1174        1183        1192        1201        1210        1219
      |           |           |           |           |           |
  GCC GAC AAC GCC CTT CCT CGC CAG TGC CAG TCT ATG ATT GAG TCT TGC TAT AGT
  Ala Asp Asn Ala Leu Pro Arg Gln Cys Gln Ser MET Ile Glu Ser Cys Tyr Ser 1228        1237        1246        1255        1264        1273
      |           |           |           |           |           |
  TCC GAG AGC GCT TGG GTT TGT GTC CCG GCC TCC ATC ATG ATT GAG TCT TGC TAT AGT
  Ser Glu Ser Ala Trp Val Cys Val Pro Ala Ser Ile MET Ile Glu Ser Tyr Ser
```

TCC GAG AGC GCT TGG GTT TGT GTC CCG GCC TCC ATC TAC TGT AAC GCC CTC
Ser Glu Ser Ala Trp Val Cys Val Pro Ala Ser Ile Tyr Cys Asn Ala Leu

FIG. 2
(5 OF 6)

| 1282 | 1291 | 1300 | 1309 | 1318 | 1327 |
|------|------|------|------|------|------|
| CTT  | GCC  | CCT  | TAC  | CAG  | AAC  | GGA | CAG | AAC | GTC | TAC | GAT | GTT | CGT | GGT | AAG | TGC |
| Leu  | Ala  | Pro  | Tyr  | Gln  | Arg  | Thr | Gly | Gln | Asn | Val | Tyr | Asp | Val | Arg | Gly | Lys | Cys |

| 1336 | 1345 | 1354 | 1363 | 1372 | 1381 |
|------|------|------|------|------|------|
| GAG | GAT | AGC | TCC | AAC | CTC | TGC | TAC | TCG | GCC | ATG | GGC | TAC | GTC | AGC | GAC | TAC | CTG |
| Glu | Asp | Ser | Ser | Asn | Leu | Cys | Tyr | Ser | Ala | MET | Gly | Tyr | Val | Ser | Asp | Tyr | Leu |

| 1390 | 1399 | 1408 | 1417 | 1426 | 1435 |
|------|------|------|------|------|------|
| AAC | AAG | ACC | GAG | GTC | ATT | GAG | GCT | GTT | GGC | GCT | GAG | GTC | AAC | GGC | TAC | GAC | TCG |
| Asn | Lys | Thr | Glu | Val | Ile | Glu | Ala | Val | Gly | Ala | Glu | Val | Asn | Gly | Tyr | Asp | Ser |

| 1444 | 1453 | 1462 | 1471 | 1480 | 1489 |
|------|------|------|------|------|------|
| TGC | AAC | TTT | GAC | ATC | AAC | CGC | AAC | TTC | CTC | TTC | CAC | GGT | GAC | TGG | ATG | AAG | CCC |
| Cys | Asn | Phe | Asp | Ile | Asn | Arg | Asn | Phe | Leu | Phe | His | Gly | Asp | Trp | MET | Lys | Pro |

| 1498 | 1507 | 1516 | 1525 | 1534 | 1543 |
|------|------|------|------|------|------|
| TAC | CAC | CGT | CTC | GTT | CCG | GGA | CTC | CTG | GAG | CAG | ATC | CCT | GTC | CTG | ATC | TAC | GCT |
| Tyr | His | Arg | Leu | Val | Pro | Gly | Leu | Leu | Glu | Gln | Ile | Pro | Val | Leu | Ile | Tyr | Ala |

| 1552 | 1561 | 1570 | 1579 | 1588 | 1597 |
|------|------|------|------|------|------|
| TAC | CAC | ATC | TGC | AAC | TGG | CTG | GGC | AAC | AAG | GCC | TGG | ACT | GAA | GCC |
| Tyr | His | Ile | Cys | Asn | Trp | Leu | Gly | Asn | Lys | Ala | Trp | Thr | Glu | Ala |

| 1552 | 1561 | 1570 | 1579 | 1588 | 1597 |
|------|------|------|------|------|------|
| GGT | GAC | GCC | GAT | TTC | ATC | TGC | AAC | TGG | CTG | GGC | AAC | AAG | GCC | TGG | ACT | GAA | GCC |
| Gly | Asp | Ala | Asp | Phe | Ile | Cys | Asn | Trp | Leu | Gly | Asn | Lys | Ala | Trp | Thr | Glu | Ala |

FIG. 2
(6 OF 6)

```
     1606            1615       1624       1633       1642       1651
     |   |    |    |    |    |    |    |    |    |    |    |    |
     CTT GAG TGG CCC GGA CAG GCT GAA TAT GCC TCC GCT AAG CTG GAG GAC CTG GTC
     Leu Glu Trp Pro Gly Gln Ala Glu Tyr Ala Ser Ala Lys Leu Glu Asp Leu Val 1660            1669       1678       1687       1696       1705
     |   |    |    |    |    |    |    |    |    |    |    |    |
     GTG GTC GAG AAT GAG CAC AAG AAG GGC ATC GGC CAG GTC CAG GTC AAG TCC CAT GGC
     Val Val Glu Asn Glu His Lys Lys Gly Ile Gly Gln Val Gln Val Lys Ser His Gly 1714            1723       1732       1741       1750       1759
     |   |    |    |    |    |    |    |    |    |    |    |    |
     AAC TTC ACC TTC ATG CGT CTC TAT GGC GGT GGC CAC ATG GTC CCG ATG GAC CAA
     Asn Phe Thr Phe MET Arg Leu Tyr Gly Gly Gly His MET Val Pro MET Asp Gln 1768            1777       1786       1795       1804       1813
     |   |    |    |    |    |    |    |    |    |    |    |    |    ^
     CCC GAG TCG AGT CTT GAA TTC TTC AAC CGC TGG TTG GGA GGT GAA TGG TTT TAA
     Pro Glu Ser Ser Leu Glu Phe Phe Asn Arg Trp Leu Gly Gly Glu Trp Phe 1823       1833       1843       1853       1863       1873       1883
     AGACGTGCTA TCACCGCATA TAGACTTTCC GGTCATTTCG GTGACACTGC AGATATGTTT CTTAACGATA 1893       1903       1913       1923       1933       1943       1953
     GTTTGAGGAT GCTTGTCAAT GCCCACTAAT CCCGAGCCTT ATGTTACATG GTATCTATGA GTTTGTCATT 1963       1973       1983       1993       2002
     ATAGTGCATT ATGCATTTGT ACTCCGTACG AGAATGAATC AGCGGCCGC
```

Construct for the disruption of CPY

= A. niger CPY gene
= A. oryzae pryG

* # in parentheses correspond to base pairs in CPY fragment.

GENE ENCODING CARBOXYPEPTIDASE OF *ASPERGILLUS NIGER*

FIELD OF THE INVENTION

The present invention relates to a gene encoding a fungal vacuolar protease. In particular, the invention relates to a carboxypeptidase gene of a filamentous ascomycete or deuteromycete fungus, such as those of the genus Aspergillus.

BACKGROUND OF THE INVENTION

The fungal vacuole is an acidic organelle that contains many hydrolases, including several proteases, and is essentially equivalent to the mammalian lysosome. Several of the hydrolases have been identified and characterized in one or more species of fungi, particularly in yeast; these include protease A(PEP4 or PrA), protease B(PrB), aminopeptidase(APE), dipeptidyl aminopeptidase B(DPAP B), carboxypeptidase Y(CPY), and carboxypeptidase S(CPS). Most of the vacuolar hydrolases are glycoproteins which are synthesized as inactive precursors. In fact, all the aforementioned proteases with the exception of APE have signal peptides that lead to transit through the secretory pathway. In the late golgi, vacuolar proteins are sorted from secretory proteins and eventually delivered to the vacuole. In addition to a signal peptide, most vacuolar proteins also have a propeptide which is cleaved upon delivery to the vacuole to generate the mature active enzyme. It has been demonstrated that the amino acid information in PrA and CPY required for vacuolar targeting is present within the propeptide(Johnson et al., Cell 48: 875–885, 1987; Rothman et al. PNAS USA 83: 3248–3252, 1989; Valls et al., Cell 48: 887–897, 1989; Valls et al. J. Cell Biol. 111: 361–368, 1987). For CPY a string of four amino acid residues (QRPL) has been shown to be required for localization to the vacuole (Valls et al., J. Cell Biol. 111: 361–368, 1990). Once delivered to the vacuole, proteinase A (pep4)cleaves the propeptide of CPY and PrB leading to the activation of the proteases (Ammerer et al., Mol. Cell. Biol. 6: 2490–2499, 1986; Woolford et al., Mol. Cell. Biol. 6: 2500–2510, 1986).

In *S. cerevisiae*, three classes of mutants which mislocalize or missort vacuolar proteins have been identified (Bankaitis et al., PNAS USA 83: 9075–9079, 1986; Robinson et al., Mol. Cell. Biol., 8: 4936–4948, 1988; Rothman et al.,EMBO J. 8: 2057–2065, 1989; Rothman and Stevens, Cell 47: 1041–1051, 1986). These mutants are called vps or vacuolar protein sorting mutants. Several of these mutants are isolated using a selection based on the observation that overexpression of a vacuolar protease due to a high copy number on a plasmid leads to a secretion of vacuolar proteases (Stevens et al., J. Cell Biol. 102: 1551–1557, 1986; Rothman et al, PNAS USA 83: 3248–3242, 1986). This suggests that it is possible to saturate the sorting machinery within the late golgi.

In *S. cerevisiae*, it has also been demonstrated that strains deleted for PEP4, CPY and PrB produce higher levels of heterologous proteins due to a decrease in proteolysis of the desired product. Therefore, the vacuolar proteases in question are important from a commercial point of view because many of the fungi which produce them are used for recombinant production of heterologous proteins. The presence of these proteases in fermentation is undesirable, in that they can degrade the protein of interest, thereby significantly reducing yield. Elimination of the function of any given protease is facilitated by the disruption or deletion of the gene encoding it; however, doing so first requires identification and isolation of the corresponding gene in the host species of interest. As noted above, a few such genes have been isolated from various yeast strains; however, the genes encoding vacuolar proteases in the filamentous ascomycetes or deuteromycetes are less well known. For example, PEP-C(Frederick et al., Gene 125: 57–64, 1993) and PEPE (Jarai et al., Gene 145: 171–178, 1994) genes coding for two other vacuolar proteases from *Aspergilus niger* have been isolated. PEPC codes for a proteinase B(PrB) homologue, and PEPE codes for a proteinase A homologue. The gene PEP4 from *Neurospora crassa* coding for a PrA homologue has also been cloned(Bowman, 17th Fungal Genetics Conference, 1993). For the first time herein is described the gene encoding a vacuolar CPY from a filamentous ascomycete or deuteromycete.

SUMMARY OF THE INVENTION

The present invention relates to a nucleic acid construct comprising a sequence encoding a filamentous ascomycete or deuteromycete carboxypeptidase Y, as well as the recombinantly produced protein encoded thereby. As used herein, "nucleic acid construct" is intended to indicate any nucleic acid molecule of cDNA, genomic DNA, synthetic DNA or RNA origin. The term "construct" is intended to indicated a nucleic acid segment which may be single-or double-stranded, and which may be isolated in complete or partial form from a naturally occurring gene or which has been modified to contain segments of DNA which are combined and juxtaposed in a manner which would not otherwise exist in nature. The construct may optionally contain other nucleic acid segments. In a preferred embodiment, the sequence encodes a carboxypeptidase of the genus Aspergillus. The invention also provides a method for producing a non-carboxypeptidase-producing filamentous ascomycete or deuteromycete cell, which comprises disrupting or deleting the carboxypeptidase gene so as to prevent the expression of a functional enzyme, or treating the gene by classical mutagenesis using physical or chemical treatments to generate cells which are reduced or lacking in their ability to produce CPY. In addition, the invention also encompasses a filamentous ascomycete or deuteromycete which is unable to produce a functional carboxypeptidase enzyme, or which produces the carboxypeptidase in reduced amounts relative to the amount produced by the wild-type strain. Such organisms provide the basis for an improved method of recombinant protein production, wherein the carboxypeptidase-deficient microorganism is transformed with the nucleic acid construct encoding the protein of interest, and cultured under conditions conducive to the expression of the protein.

BRIEF DESCRIPTION OF THE FIGURES

FIG. 1 illustrates the DNA sequence and translation of the *A. niger* Bo-1 genomic CPY clone.

FIG. 2 illustrates the DNA sequence and translation of *A. niger* SFAG 2 CPY cDNA. The predicted site for signal peptidase cleavage and the N-terminus of mature CPY are indicated.

DETAILED DESCRIPTION OF THE INVENTION

Figure 3:
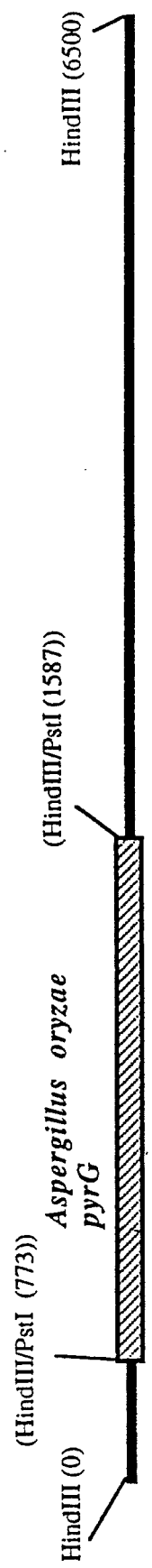
FIG. 3 illustrates the construct used in disruption CPY.

Attempts to isolate an Aspergillus carboxypeptidase Y are initiated by designing a series of degenerate oligonucleotides, using the sequences of *S. cerevisiae* CPY, *Penicillium*

*janthinellum* carboxypeptidase S1(Svedsen et al., FEBS 333: 39–43, 1993, and malt carboxypeptidase-MIII(Sørensen et al., Carlsberg Res. Commun. 54: 193–202, 1993). The oligonucleotide sequences are provided the examples below. These sequences are used as primers in various combinations in a PCR reaction using *Aspergillus niger* strain Bo-1 genomic DNA as a template. Two of the reactions(with primers 1-1 and 2-1; and 1-2 and 2-2) yield an 1100 bp amplification product, which is subcloned and sequenced, but none of the subclones has significant homology to CPY to be identified as the gene of interest.

Further PCR reactions with primers 3-1, 3-2, 4-1, 4-2, 2-1 and 2-2 are then made. In two of the reactions(primers 4-1 and 2-1; and 4-2 and 2-1) a 600bp amplification product is obtained. This product is subcloned and 11 of the subclones sequenced; nine of these subclones are identical, and have homology to carboxypeptidaseY genes from other sources. The insert from one of the subclones is used to probe *A. niger* genomic DNA; hybridization with single bands is observed with BamHI. HindIII, and SalI digests, suggesting that a single CPY gene exists in *A. niger.* Hybridizations are done at 65° C. in 1.5×SSPE, 1.0% SDS, 0.5% non-fat milk and 200 µg/ml salmon sperm DNA.

An *A. niger* genomic DNA bank in EMBL4 is prepared and probed with the PCR CPY-derived gene fragment($^{32}$P-labeled), in order to isolate a full length gene. Out of approximately 28,000 plaques, 11 positives are picked; nine of these still hybridize with the probe after purification. A 5.5 HindIII fragment common to a majority of these clones is identified as the *A. niger* CPY gene. This fragment is subcloned and sequenced; the sequence of the fragment, including the CPY coding region and predicted amino acid sequence, is provided in FIG. 1.

Subsequently, a cDNA bank from a different *A. niger* strain is also screened. At least one full-length clone is identified from this library as well. This clone is sequenced and the sequence is depicted in FIG. 2. Both DNA sequences predict a CPY precursor of 557 amino acids in length. Based on a comparison with the homologous gene from *S. cerevisiae*, CPY from *A. niger* appears to have a pre-propeptide of 137 or 138 amino acids. The gene contains one intron of 61 base pairs. A comparison of the two *A. niger* sequences will show some difference in amino acid sequence, which presumably reflects the different strains from which the genomic and cDNA clones are isolated. A comparison with the amino acid sequences of the corresponding CPY genes of *S. cerevisiae* and *C. albicans* shows a 65% and 66% identity, respectively.

The present invention is not limited to the use of the sequences disclosed in FIGS. 1 and 2. First, the invention also encompasses nucleotide sequences which produce the same amino acid sequence as depicted in FIG. 1 or 2, but differ by virtue of the degeneracy of the genetic code. In addition, the difference in amino acid sequence shown for two strains of the same species shows that variation within the sequence of a single species is tolerated, and using the techniques described herein, such variants can readily be identified. Therefore, when "*A. niger*" is referred to in this context, it will be understood to encompass all such variations. In particular, the invention also encompasses any variant nucleotide sequence, and the protein encoded thereby, which protein retains at least about an 80%, preferably about 85%, and most preferably at least about 90–95% homology with the amino acid sequence depicted in FIG. 1 or 2, and which qualitatively retains the activity of the sequence described herein. Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln.

In addition, the isolated gene provides a means for isolating homologous genes from other filamentous ascomycetes or deuteromycetes, such as other Aspergillus species, e.g., *A. oryzae, A. foetidus, A. japonicus, A. aculeatus*, or *A. nidulans*. Other non-Aspergillus filamentous ascomycete species include Fusarium species, such as *F. graminearum, F. oxysporum, F. solani, F. culmorum* (or corresponding teleomorphs) *Neurospora crassa, Trichoderma reesei, T. viridae, T. harzianum, T. longibranchiatum, Penicillium janthinellum, P. notatum, P. chrysogenum, P. camemberti, P. roqueforti, Humicola insolen, H. grisea var. thermoidea, H. lanuginosa, Scycalidium thermophilum, Myceliophthora thermophila*, and *Thielavia terrestris*. The gene, or an oligonucleotide based thereon, can be used as probes in southern hybridization to isolate homologous genes of these other species. In particular, such probes can be used under low to high stringency conditions(for example, prehybridization and hybridization at 42° C. in 5×SSPE, 0.3% SDS, 200 µg/ml sheared and denatured salmon sperm DNA, and either 50, 35 or 25% formamide for high, medium and low stringencies, respectively) for hybridization with the genomic or cDNA of the species of interest, following standard southern blotting procedures, in order to identify and isolate the corresponding CPY gene therein. A PCR reaction using the degenerate probes mentioned herein and genomic DNA or first-strand cDNA from a filamentous fungus may also yield a CPY-specific product which could then be used as a probe to clone the corresponding genomic or cDNA.

The present gene is particularly useful in the creation of carboxypeptidase-deficient mutants of filamentous ascomycetes such as Aspergillus. This can be achieved in a number of ways. In one method, as described in further detail below, a selectable marker is cloned into the middle of the CPY gene. The disrupted fragment is then released from the parental plasmid using restriction enzymes. The linearized DNA fragment is used to transform the chosen host cell. In the host cell, the homologous ends pair with the host cell chromosome, and the homologous recombination results in a chromosomal gene replacement. Useful selectable markers for use with fungal cell hosts include amdS, pyrG, argB, niaD, sC, and hygB. Alternately, a two-step process can be employed using a two-way selectable marker. In such a process, a plasmid containing a truncated CPY gene and the selectable marker gene is digested with a restriction enzyme which cuts once within the the CPY fragment in order to target integration to the CPY locus during transformation. The transformants are then grown on media which will select for the loss of the selectable marker gene, e.g., when the marker is pyrG, the medium may contain 5-fluorootic acid. The loss of the selectable gene usually occurs by a recombination between the wild type CPY and the introduced truncated CPY gene. Approximately 50% of the resulting strain should have only the truncated CPY gene while the other 50% will contain only the wild type gene. Such methods are described in Rothstein, Meth. Enzymol. 194, 281–301, 1991.

The CPY-deficient mutants so created are particularly useful in the expression of heterologous protein. By "heterologous protein" in the present context is meant a protein which is not native to the host cell, a native protein in which modifications have been made to alter the native sequence, or a native protein whose expression is quantitatively altered as a result of a manipulation of the host cell by recombinant DNA techniques. Also encompassed within this term are native proteins for which expression in the mutants involves the use of genetic elements not native to the host cell, or use of native elements which have been manipulated to function in a manner not normally seen in the host cell.

As already noted, the production of proteases by a chosen host cell can severely limit the yield of the desired protein by degrading the product before it can be recovered. The elimination or reduction in the amount of CPY produced by a host can therefore substantially increase the yield of any given protein, and can render an otherwise commercially unsuitable host cell commercially feasible for recombinant protein production. In a preferred embodiment, the CPY deficient cells produce at least 25% less, preferably at least 50% less, and most preferably at least 70% less CPY, up to total loss of CPY function, than the corresponding wild-type strain.

The mutant fungal cells of the present invention can be used in recombinant protein production in the same manner as the wild-type strains. Those skilled in the art will readily recognize routine variations from the specific embodiments described herein which are useful in adapting the methodology to the strains noted above. A gene of interest can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein, nucleotides encoding a signal sequence may be inserted prior to the coding sequence of the gene. For expression under the direction of control sequences, a gene to be used according to the invention is operably linked to the control sequences in the proper reading frame.

The expression vector may be any vector which may conveniently be subjected to recombinant DNA procedures, and the choice of vector will typically depend on the host cell into which it is to be introduced. In a preferred embodiment of the present invention, the host cell is a strain of the genus Aspergillus. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the sequence of the gene of interest should be operably connected to a suitable promoter sequence. The promoter may be any DNA sequence which shows transcriptional activity in the host cell of choice and may be derived from genes encoding proteins either homologous or heterologous to the host cell. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (glaA), *Rhizomucor miehei* lipase, *A. oryzae* alkaline protease, *A. oryzae* triose phosphate isomerase or *A. nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the heterologous gene sequence. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, or one which confers antibiotic resistance such as ampicillin, kanamycin, chloramphenicol or tetracycline resistance. Examples of Aspergillus selection markers include amdS, pyrG, argB, niaD, sC, and hygB, a marker giving rise to hygromycin resistance. Preferred for use in an Aspergillus host cell are the amdS and pyrG markers of *A. nidulans* or *A. oryzae*. Furthermore, selection may be accomplished by co-transformation, e.g. as described in WO 91/17243.

It is generally preferred that the expression gives rise to a product which is extracellular. The protein of interest may thus comprise a preregion permitting secretion of the expressed protein into the culture medium. If desirable, this preregion may be native to the protein of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei*, the gene for the α-factor from *Saccharomyces cerevisiae* or the calf preprochymosin gene. Particularly preferred, when the host is a fungal cell, is the preregion for *A. oryzae* TAKA amylase, *A. niger* neutral amylase, the maltogenic amylase form Bacillus NCIB 11837, *B. stearothermophilus* α-amylase, or *Bacillus licheniformis* subtilisin. An effective signal sequence is the *A. oryzae* TAKA amylase signal, the *Rhizomucor miehei* aspartic proteinase signal and the *Rhizomucor miehei* lipase signal.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Molecular Cloning, 1989).

The CPY-deficient mutants can be used to express any prokaryotic or eukaryotic protein of interest, and are preferably used to express eukaryotic proteins. Of particular interest for these cells is their use in expression of fungal enzymes such as catalase, laccase, phenoloxidase, oxidase, oxidoreductases, cellulase, xylanase, peroxidase, lipase, hydrolase, esterase, cutinase, protease and other proteolytic enzymes, aminopeptidase, carboxypeptidase, phytase, lyase, pectinase and other pectinolytic enzymes, amylase, glucoamylase, α-galactosidase, galactosidase, β-glucosidase, α-glucosidase, β-glucosidase, mannosidase, isomerase, invertase, transferase, ribonuclease, chitinase, and deoxyribonuclease. It will be understood by those skilled in the art that the term "fungal enzymes" includes not only native fungal enzymes, but also those fungal enzymes which have been modified by amino acid substitutions, deletions, additions, or other modifications which may be made to enhance activity, thermostability, pH tolerance and the like. The mutants can also be used to express heterologous proteins of pharmaceutical interest such as hormones, growth factors, receptors, and the like.

The invention will be further illustrated by the following non-limiting examples.

EXAMPLES

I. ISOLATION OF THE *ASPERGILLUS NIGER* CPY GENE

A. MATERIALS AND METHODS i. Strains.

The following biological materials are used in the procedures described below. *Escherichia coli* K802 (ek4(nrca), mcrB, hsdR2, galK2, GalT22, supE44, metB1; *E. coli* SOLR (E14- (mcrA)Δ(mcrCB-hsdSMR-mr$^r$) 171, sbcC, recB, recJ, uvrC, umuC::Tn5(kan$^r$), lac, gyrA96, relA1, thi-1, endA1, λ$^R$[F'proABlaCI$^q$ZΔM15]Su$^-$, *E. coli* JM101supE, thi-1, Δ(lac-proAB), [F'traD36, proAB, lacI$^q$ZΔM15], *E. coli* XL-1 Blue recA1, endA1, gyrA96, thi-1, hsdR17, supE44, relA1, lac, [F'proAB, lacI$^q$ZΔM15, Tn10 (tet$^R$)], *Aspergillus niger* Bo-1, *A. niger* SFAG-2.

ii. PCR amplification.

PCR reactions are run using standard protocols with annealing steps done at 45° C. *A. niger* Bo-1 genomic DNA is used as template and the following degenerate oligonucleotides are used.

Primer 1-1(94-282)-GGIGGICCIGGITGYTC
Primer 1-2(94-283)-GGIGGICCIGGITGYAG
Primer 2-1(94-284)-CCIAGCCARTTRCADAT
Primer 2-2(94-285)-CCYAACCARTTRCADAT
Primer 3-1(94-331)-GTIGGITTYTCITAYTCIGG
Primer 3-2(94-332)-GTIGGITTYAGYTAYAGYGG
Primer 4-1(94-329)-GARTCITAYGCIGGICAYTA
Primer 2-1(94-284)-GARAGYTAYGCIGGICAYTA In the above primers, I stands for inosine, Y for C or T, R for A or G, and D for A, G or T.

iii. Subcloning PCR products.

PCR products are subcloned for sequencing using the TA Cloning Kit(Invitrogen) following the manufacturer's protocols.

iv. In vivo excision from Lambda Zap II.

From the CPY cDNA Lambda Zap clones, a plasmid is rescued containing the cDNA inserts in a pBluescript SK- vector by passage through the *E. coli* strain SOLR following the protocols provided by Stratagene.

v. DNA sequencing.

Nucleotide sequencing is determined using TAQ polymerase cycle-sequencing with fluorescent labeled nucleotides. The sequencing reactions are electrophoresed on an Applied Biosystems automatic DNA sequencer(Model 363A, version 1.2.0). The following CPY specific primers are used, in addition to the M13 reverse(−48) and M13(−20) forward primers(Sanger et al., J. Mol. Biol. 143: 163–178):

| | |
|---|---|
| 94-376 | TCGCTGCCAGTCTATGATTGA |
| 94-377 | ACATCAACCGCAACTTCCTCT |
| 94-378 | TTGCCAATGAGAACGGACTGC |
| 94-379 | CGCACTTACCACGGACATCAT |
| 94-503 | CAAGCATCCTCAAACTATCGT |
| 94-504 | GAGACGCATGAAGGTGAAGTT |
| 94-505 | GCCGTCCCTCCCTTCCAGCAG |
| 94-506 | GTGCCGACGGGTTCTCCAAGC |
| 94-507 | GCAGCGAGGAAGAGCGTTGTC |
| 94-510 | GGGTCATTCTCGGGGTCATTG |
| 94-511 | GACCCCGAGAATGACCCTGTT |
| 94-512 | GTAGGGCTTCATCCAGTCACC |
| 94-513 | TCTCACCGTTCTCACCAGTAA |
| 94-514 | TCCCTCCCCAAGAAGCACAAC |
| 94-528 | AGCGTCTGGGTTACTGGTGAG |
| 94-529 | AAGATCGGCCAGGTCAAGTCC |
| 94-530 | GAGACGGTGGTAGGGCTTCAT |
| 94-531 | AACGTCGGTTACTCTTACAGC |
| 94-532 | GTGGTCGGGGCGGCGGTTGTG |
| 94-533 | TGTTTGAAGAAGAGGGTAAGC |
| 94-575 | CGCTGCTACTTGATTTTTCTA |
| 94-576 | CTCAGCGCCAACAGCCTCAAT |
| 94-577 | ACCTGCAGTCCGTTCTTATTG |
| 94-634 | TGCGATCGATTCATTCTCATC |
| 94-635 | GGAGTAACCGACATTGACAGG |
| 94-636 | CCTGTCAATGTCGGTTACTCC |
| 94-637 | GTCCCATGGCAACTTCACCTT |
| 94-646 | CTTCTCACCGTTCTCACCAGT |
| 94-647 | CGAGACTCGAAGAACCCTAAG |

B. RESULTS

Using *A. niger* Bo-1 genomic DNA as template PCR reactions are done using various combinations of the CPY specific degenerate oligonucleotides, primers 1-1, 1-2, 2-1, and 2-2(FIG. 1). All reactions are done using one cycle at 95° C. for 5 minutes, 45° C. for 1 minute and 72° C. for 2 minutes followed by 25 cycles at 95° C. for 1 minute, 45° C. for one minute and 72° C. for 2 minutes. Aliquots(10 μl) of the reactions were electrophoresed on an agarose gel, and in two of the reactions, one with primers 1-2 and 2-1 and one with primers 1-2 and 2-2, an amplification product of approximately 1100 bp is the major species. The predicted size of a product using these oligonucleotide combinations assuming there are no introns within the gene is 900 bp. the 1100 bp amplification product is subcloned and sequenced using the forward and reverse primers. Seven of the subclones are sequenced; however, none of them by homology code for CPY.

PCR reactions using various combinations of primers 3-1, 3-2, 4-1, 4-2, 2-1 and 2-2 are run using the same conditions as above. Aliquots are electrophoresed on an agarose gel, and in two of the reactions, one with primers 4-1 and 2-1 and one with primers 4-2 and 2-1, an amplification product of approximately 600 bp is the major species. The expected size for this amplification product based on homology to other carboxypeptidases is 600 bp. The 600 bp amplification product is subcloned and the DNA sequence is determined for 11 of the subclones using the forward and reverse primers. Nine of the 11 subclones, based on identity of 69% to *S. cerevisiae*, code for CPY from *A. niger*. All 9 are identical to one another suggesting there is only one gene for carboxypeptidase in *A. niger*. The subclone containing the *A. niger* CPY PCR product of 600 bp is designated pDSY17.

A Southern blot of *A. niger* Bo-1 genomic DNA is probed with the insert from pDSY17. The probe is radiolabeled using a nick-translation kit from Gibco-BRL. Hybridization conditions used are 60° C. in 1.5×SSPE, 1% SDS, 0.5% nonfat milk and 200 μg/ml salmon sperm DNA. The blot is washed at 65° C. for 15 minutes twice in 0.2×SSC, 1% SDS and 0.1% Na pyrophosphate. In the BamHI, HindIII and SAII digests, single bands of approximately 10, 5.5 and 7 kb, respectively hybridize to the CPY probe.

In order to isolate the full gene for CPY, a genomic bank in EMBL4 of *A. niger* Bo-1 containing approximately 26,000 recombinants is probed with the PCR-derived CPY gene fragment, radiolabeled with the Gibco-BRL nick translation kit. Approximately 28,000 plaques are lifted to filters and probed. Eleven positives from these plates are picked. After purification, 9 of the primary clones still hybridized with the CPY probe. DNA is isolated from the 9 clones, and restriction digests are done in order to begin characterizing them. From the restriction patterns, 7 of the 9 are identical. The other two clones are unique. From Southern digests of the clones, it is determined that 8 of the 9 have the same HindIII fragment of approximately 5.5 kb which hybridizes to the CPY probe. The clone which does not contain the same HindIII fragment contains a larger (>12 kb) HindIII fragment which hybridizes to the CPY probe. The common HindIII fragment is subcloned for DNA sequencing. The genomic DNA sequence and predicted amino acid sequence is shown in FIG. 1.

A cDNA bank in Lambda ZAPII(Stratagene) of *A. niger* SFAG-2 is also screened. Approximately 42,000 plaques are lifted to filter and probed with the CPY probe as above, and 112 of these plaques appear to hybridize under the stringent conditions defined above. Twenty of the initial positives are picked and rescreened, and upon purification, 18 still hybridize with the CPY probe. From 4 of the positive clones, DNA is isolated using the in vivo excision protocol provided with the Lambda Zap kit. The rescued plasmids are digested with EcoRI and electrophoresed on an agarose gel to determine the sizes of the inserts. Two of the clones(2-1 and 3-2) appear to have large enough inserts to contain the full length cDNA for CPY, and each contains two EcoRI fragments of approximately 1700 and 250 bp. The predicted size for a full length cDNA is approximately 1600 bp. The other two cDNA clones (2-2 and 2-4) have smaller inserts; however, they all contain the 250 bp EcoRI fragment. Partial DNA sequences of clones 3-2 and 2-2 are determined, and 3-2 contains the full-length cDNA while clone 2-2 is truncated at the 5' end by about 200 bp.

The complete cDNA sequence is determined on both strands(FIG. 2). The cDNA is predicted to code for a CPY precursor of 557 amino acids in length. To date most of the nucleotide differences found between the cDNA and genomic clones are within the wobble which is not surprising since they come from two different *A. niger* strains. Based on an alignment with CPY from *S. cerevisiae*, CPY from *A. niger* appears to have both a signal peptide and a propeptide and the mature CPY protein is either 419 or 420 amino acids in length. *A. niger* CPY has approximately 65% and 66% identity to CPY from the yeasts *S. cerevisiae* and *C. albicans* (Mukhtar et al., Gene 121: 173–177, 1992), respectively.

II. PREPARATION OF A CPY-DEFICIENT MUTANT.

In order to create an *A. niger* strain deleted for CPY, a construct in whichthe *A. oryzae* pyrG gene is inserted into the coding region of CPY is made(FIG. 3). An ~6.5 kb HindIII fragment containing almost the entire gene of CPY and ~6kb downstream of the gene is subcloned into a pKS+(Stratagene) derivative in which the PstI site has been destroyed. The resulting recombinant is digested with PstI to delete an 815 bp fragment from the CPY coding region, and the overhangs created by digestion with PstI are blunted by the addition of T4 DNA polymerase and all 4 dNTPs. The resulting blunt-end vector is ligated to an ~3.8 kb blunt-end fragment obtained by digestion with HindIII followed by a fill-reaction using Klenow fragment. The final construct in which the CPY gene has the pyrG inserted is digested with HindIII to create a linear fragment which is used to transform an *A. niger* pyrG strain selecting for growth on minimal medium plates. Transformants are screened by Southern blotting to determine which strains contain a disrupted CPY gene. The transformants are further analyzed by Western blotting to look for the absence of CPY intracellularly. Once a strain is identified as containing a disruption of CPY, the effect on heterologous protein is determined.

Deposit of Biological Materials

The following biological materials have been deposited on Sep. 13, 1994 in Agricultural Research Service Culture Collection (NRRL) 1815 North University Street, Peoria, Ill. 61604.

| Cell line | Accession No. |
|---|---|
| *E. coli* containing pDSY23 (EMCC #0120) | NRRL B-21326 |

What is claimed is:

1. A nucleic acid construct containing a nucleic acid sequence encoding an *Aspergillus niger* carboxypeptidase Y.

2. A nucleic acid construct containing the nucleic acid sequence depicted in SEQ ID NO.: 1, or a nucleic acid sequence which hybridizes with SEQ ID NO.: 1 under high stringency conditions.

3. The nucleic acid construct of claim 2 in which the nucleic acid sequence encodes a protein with the amino acid sequence depicted in SEQ ID NO.: 2.

4. A nucleic acid construct containing the nucleic acid sequence depicted in SEQ ID NO.: 3, or a nucleic acid sequence which hybridizes with SEQ ID NO.: 3 under high stringency conditions.

5. The nucleic acid construct of claim 4 in which the nucleic acid sequence encodes a protein with the amino acid sequence depicted in SEQ ID NO.: 4.

6. The construct of claim 1 in which is a selectable marker is inserted into the carboxypeptidase sequence.

7. The construct of claim 6, in which the selectable marker is amdS, pyrG, argB, niaD, sC, or hygB.

8. The construct of claim 2 in which the nucleic acid sequence which hybridizes with SEQ ID NO.: 1 is obtained from Aspergillus, Fusarium, Penicillium, Humicola, Trichoderma, Scytalidium, Myceliophthora or Thielavia.

9. The construct of claim 4 in which the nucleic acid sequence which hybridizes with SEQ ID NO.: 3 is obtained from Aspergillus, Fusarium, Penicillium, Humicola, Trichoderma, Scytalidium, Myceliophthora or Thielavia.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 2068 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Aspergillus niger ( i x ) FEATURE:
    ( A ) NAME/KEY: intron
    ( B ) LOCATION: 572..632

( i x ) FEATURE:
    ( A ) NAME/KEY: CDS
    ( B ) LOCATION: join (571..633)

( x i ) SEQUENCE DESCRIPTION: SEQ ID NO: 1:

```
TCCTCTGCCT ACTCATCCCA TCACCATCTC AATTCATACC GCCCCCGTGG GGTTTCAGCA         60

CCA ATG AGA GTC CTT CCA GCT GCT ATG CTG GTT GGA GCG GCC ACG GCG        108
    Met Arg Val Leu Pro Ala Ala Met Leu Val Gly Ala Ala Thr Ala
    1           5                   10                  15

GCC GTT CCT CCC TTC CAG CAG GTC CTT GGA GGT AAC GGT GCC AAG CAC        156
Ala Val Pro Pro Phe Gln Gln Val Leu Gly Gly Asn Gly Ala Lys His
            20                  25                  30

GGT GCC GAC CAT GCG GCC GAG GTC CCT GCG GAT CAC AGT GCC GAC GGG        204
Gly Ala Asp His Ala Ala Glu Val Pro Ala Asp His Ser Ala Asp Gly
        35                  40                  45

TTC TCC AAG CCG CTG CAC GCA TTC CAG GAG GAG CTG AAG TCT CTC TCT        252
Phe Ser Lys Pro Leu His Ala Phe Gln Glu Glu Leu Lys Ser Leu Ser
    50                  55                  60

GAC GAG GCT CGT AAG CTT TGG GAT GAG GTG GCC AGC TTC TTC CCG GAG        300
Asp Glu Ala Arg Lys Leu Trp Asp Glu Val Ala Ser Phe Phe Pro Glu
65              70                  75

AGC ATG GAT CAG AAC CCT CTC TTT TCC CTC CCC AAG AAG CAC AAC CGC        348
Ser Met Asp Gln Asn Pro Leu Phe Ser Leu Pro Lys Lys His Asn Arg
80              85                  90                  95

CGT CCC GAC TCG CAC TGG GAC CAC ATC GTC CGC GGC TCC GAC GTT CAG        396
Arg Pro Asp Ser His Trp Asp His Ile Val Arg Gly Ser Asp Val Gln
                100                 105                 110

AGC GTC TGG GTC ACT GGT GAG AAC GGT GAG AAG GAG CGC GAG GTC GAT        444
Ser Val Trp Val Thr Gly Glu Asn Gly Glu Lys Glu Arg Glu Val Asp
            115                 120                 125

GGC AAG CTG GAA GCC TAT GAT CTC AGG GTC AAG AAG ACC GAT CCT GGC        492
Gly Lys Leu Glu Ala Tyr Asp Leu Arg Val Lys Lys Thr Asp Pro Gly
        130                 135                 140

TCT CTT GGC ATC GAC CCC GGC GTG AAG CAG TAC ACC GGT TAT CTC GAT        540
Ser Leu Gly Ile Asp Pro Gly Val Lys Gln Tyr Thr Gly Tyr Leu Asp
    145                 150                 155

GAC AAC GAG AAT GAT AAG CAT TTG TTC TAC GTAAGCACAC CTTGGTTCAA          590
Asp Asn Glu Asn Asp Lys His Leu Phe Tyr
160                 165

GATCACGCTT TTTATATGCT CTGGATATCT AACGCAACTT AG TGG TTC TTC GAG         644
                                                Trp Phe Phe Glu
                                                170

TCT CGC AAT GAC CCC GAG AAT GAT CCC GTT GTT CTG TGG CTG AAC GGT        692
Ser Arg Asn Asp Pro Glu Asn Asp Pro Val Val Leu Trp Leu Asn Gly
    175                 180                 185

GGC CCT GGG TGC TCT TCC CTC ACC GGT CTC TTC ATG GAG CTT GGC CCT        740
Gly Pro Gly Cys Ser Ser Leu Thr Gly Leu Phe Met Glu Leu Gly Pro
190                 195                 200                 205

AGC AGC ATC AAC AAG AAG ATC CAG CCG GTC TAC AAT GAC TAC GCT TGG        788
Ser Ser Ile Asn Lys Lys Ile Gln Pro Val Tyr Asn Asp Tyr Ala Trp
                210                 215                 220

AAC TCC AAC GCG TCC GTG ATC TTC CTT GAC CAG CCT GTC AAT GTC GGT        836
Asn Ser Asn Ala Ser Val Ile Phe Leu Asp Gln Pro Val Asn Val Gly
            225                 230                 235

TAC TCC TAC AGT AAC TCT GCT GTC AGC GAC ACG GTC GCT GCT GGC AAG        884
Tyr Ser Tyr Ser Asn Ser Ala Val Ser Asp Thr Val Ala Ala Gly Lys
        240                 245                 250
```

```
GAC GTC TAT GCC TTG CTT ACC CTC TTC TTC AAA CAA TTC CCC GAG TAT           932
Asp Val Tyr Ala Leu Leu Thr Leu Phe Phe Lys Gln Phe Pro Glu Tyr
        255                 260                 265

GCT AAG CAG GAC TTC CAC ATT GCC GGT GAA TCT TAT GCT GGT CAC TAT           980
Ala Lys Gln Asp Phe His Ile Ala Gly Glu Ser Tyr Ala Gly His Tyr
270                 275                 280                 285

ATC CCC GTC TTC GCT TCG GAG ATC CTG TCT CAC AAG AAG CGC AAC ATC          1028
Ile Pro Val Phe Ala Ser Glu Ile Leu Ser His Lys Lys Arg Asn Ile
                290                 295                 300

AAC CTG CAG TCC GTT CTC ATT GGC AAC GGT CTC ACC GAC GGA TAC ACC          1076
Asn Leu Gln Ser Val Leu Ile Gly Asn Gly Leu Thr Asp Gly Tyr Thr
            305                 310                 315

CAG TAC GAG TAC TAC CGT CCC ATG GCC TGC GGT GAC GGC GGT TAC CCA          1124
Gln Tyr Glu Tyr Tyr Arg Pro Met Ala Cys Gly Asp Gly Gly Tyr Pro
        320                 325                 330

GCT GTC TTG GAC GAG AGC TCC TGC CAG TCC ATG GAC AAC GCT CTT CCT          1172
Ala Val Leu Asp Glu Ser Ser Cys Gln Ser Met Asp Asn Ala Leu Pro
335                 340                 345

CGC TGC CAG TCT ATG ATT GAG TCT TGC TAC AGT TCC GAG AGC GCT TGG          1220
Arg Cys Gln Ser Met Ile Glu Ser Cys Tyr Ser Ser Glu Ser Ala Trp
350                 355                 360                 365

GTT TGT GTC CCG GCC TCC ATC TAC TGT AAC AAC GCC CTC CTT GCC CCT          1268
Val Cys Val Pro Ala Ser Ile Tyr Cys Asn Asn Ala Leu Leu Ala Pro
                370                 375                 380

TAC CAG CGC ACT GGG CAG AAC GTC TAT GAT GTC CGT GGT AAG TGC GAG          1316
Tyr Gln Arg Thr Gly Gln Asn Val Tyr Asp Val Arg Gly Lys Cys Glu
            385                 390                 395

GAT AGC TCT AAC CTT TGC TAC TCG GCT ATG GGC TAC GTC AGC GAC TAC          1364
Asp Ser Ser Asn Leu Cys Tyr Ser Ala Met Gly Tyr Val Ser Asp Tyr
        400                 405                 410

CTG AAC AAG CCC GAA GTC ATC GAG GCT GTT GGC GCT GAG GTC AAC GGC          1412
Leu Asn Lys Pro Glu Val Ile Glu Ala Val Gly Ala Glu Val Asn Gly
415                 420                 425

TAC GAC TCG TGC AAC TTT GAC ATC AAC CGC AAC TTC CTC TTC CAC GGT          1460
Tyr Asp Ser Cys Asn Phe Asp Ile Asn Arg Asn Phe Leu Phe His Gly
430                 435                 440                 445

GAC TGG ATG AAG CCC TAC CAC CGC CTC GTT CCG GGA CTC CTG GAG CAG          1508
Asp Trp Met Lys Pro Tyr His Arg Leu Val Pro Gly Leu Leu Glu Gln
                450                 455                 460

ATC CCT GTC TTG ATC TAT GCC GGT GAT GCT GAT TTC ATT TGC AAC TGG          1556
Ile Pro Val Leu Ile Tyr Ala Gly Asp Ala Asp Phe Ile Cys Asn Trp
            465                 470                 475

CTG GGC AAC AAG GCC TGG ACT GAA GCC CTG GAG TGG CCC GGA CAG GCT          1604
Leu Gly Asn Lys Ala Trp Thr Glu Ala Leu Glu Trp Pro Gly Gln Ala
        480                 485                 490

GAA TAT GCC TCC GCT GAG CTG GAG GAT CTG GTC ATT GTC GAC AAT GAG          1652
Glu Tyr Ala Ser Ala Glu Leu Glu Asp Leu Val Ile Val Asp Asn Glu
495                 500                 505

CAC ACG GGC AAG AAG ATT GGC CAG GTT AAG TCC CAT GGC AAC TTC ACC          1700
His Thr Gly Lys Lys Ile Gly Gln Val Lys Ser His Gly Asn Phe Thr
510                 515                 520                 525

TTC ATG CGT CTC TAT GGT GGT GGC CAC ATG GTC CCG ATG GAC CAG CCC          1748
Phe Met Arg Leu Tyr Gly Gly Gly His Met Val Pro Met Asp Gln Pro
                530                 535                 540

GAG TCG AGT CTC GAG TTC TTC AAC CGC TGG TTG GGA GGT GAA TGG TTC          1796
Glu Ser Ser Leu Glu Phe Phe Asn Arg Trp Leu Gly Gly Glu Trp Phe
            545                 550                 555

TAA AGACGTGCTA CCACCGCATA TAGACTTTCT GGTCATTTCG GTGACACTGC              1849

AGATATGTTT CTTAACGATA GTTTGAGCAT GCTTGTCAAT GCCCACTAGT CCCGATCCTT       1909
```

```
ATATGTTGCA  TGGTATCTAT  GAGTTTTGTC  ACTATAGTGC  ATTATACATG  TGTACTTCGT   1969

ATGAGAATGA  ATCGATCGCA  TTTACACGCA  TATAAATAGT  ACCCACCTCC  GCCTGGACAT   2029

GAATTAGGCC  CGGCCAGTCG  TTTACATACA  GTGCTAGAA                            2068
```

( 2 ) INFORMATION FOR SEQ ID NO: 2:

( i ) SEQUENCE CHARACTERISTICS:
        ( A ) LENGTH: 557 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Aspergillus Niger ( x i ) SEQUENCE DESCRIPTION: SEQ ID NO: 2:

```
Met  Arg  Val  Leu  Pro  Ala  Ala  Met  Leu  Val  Gly  Ala  Ala  Thr  Ala  Ala
 1             5                        10                       15

Val  Pro  Pro  Phe  Gln  Gln  Val  Leu  Gly  Gly  Asn  Gly  Ala  Lys  His  Gly
               20                       25                       30

Ala  Asp  His  Ala  Ala  Glu  Val  Pro  Ala  Asp  His  Ser  Ala  Asp  Gly  Phe
          35                       40                       45

Ser  Lys  Pro  Leu  His  Ala  Phe  Gln  Glu  Glu  Leu  Lys  Ser  Leu  Ser  Asp
 50                       55                       60

Glu  Ala  Arg  Lys  Leu  Trp  Asp  Glu  Val  Ala  Ser  Phe  Phe  Pro  Glu  Ser
 65                  70                       75                       80

Met  Asp  Gln  Asn  Pro  Leu  Phe  Ser  Leu  Pro  Lys  Lys  His  Asn  Arg  Arg
               85                       90                       95

Pro  Asp  Ser  His  Trp  Asp  His  Ile  Val  Arg  Gly  Ser  Asp  Val  Gln  Ser
              100                      105                      110

Val  Trp  Val  Thr  Gly  Glu  Asn  Gly  Glu  Lys  Glu  Arg  Glu  Val  Asp  Gly
              115                      120                      125

Lys  Leu  Glu  Ala  Tyr  Asp  Leu  Arg  Val  Lys  Lys  Thr  Asp  Pro  Gly  Ser
130                       135                      140

Leu  Gly  Ile  Asp  Pro  Gly  Val  Lys  Gln  Tyr  Thr  Gly  Tyr  Leu  Asp  Asp
145                       150                      155                      160

Asn  Glu  Asn  Asp  Lys  His  Leu  Phe  Tyr  Trp  Phe  Phe  Glu  Ser  Arg  Asn
                    165                      170                      175

Asp  Pro  Glu  Asn  Asp  Pro  Val  Val  Leu  Trp  Leu  Asn  Gly  Gly  Pro  Gly
                    180                      185                      190

Cys  Ser  Ser  Leu  Thr  Gly  Leu  Phe  Met  Glu  Leu  Gly  Pro  Ser  Ser  Ile
               195                      200                      205

Asn  Lys  Lys  Ile  Gln  Pro  Val  Tyr  Asn  Asp  Tyr  Ala  Trp  Asn  Ser  Asn
210                       215                      220

Ala  Ser  Val  Ile  Phe  Leu  Asp  Gln  Pro  Val  Asn  Val  Gly  Tyr  Ser  Tyr
225                       230                      235                      240

Ser  Asn  Ser  Ala  Val  Ser  Asp  Thr  Val  Ala  Ala  Gly  Lys  Asp  Val  Tyr
                    245                      250                      255

Ala  Leu  Leu  Thr  Leu  Phe  Phe  Lys  Gln  Phe  Pro  Glu  Tyr  Ala  Lys  Gln
               260                      265                      270

Asp  Phe  His  Ile  Ala  Gly  Glu  Ser  Tyr  Ala  Gly  His  Tyr  Ile  Pro  Val
          275                      280                      285

Phe  Ala  Ser  Glu  Ile  Leu  Ser  His  Lys  Lys  Arg  Asn  Ile  Asn  Leu  Gln
290                       295                      300
```

| | | | | | | | | | | | | | | |
|---|---|---|---|---|---|---|---|---|---|---|---|---|---|---|
| Ser 305 | Val | Leu | Ile | Gly 310 | Asn | Gly | Leu | Thr | Asp 315 | Gly | Tyr | Thr | Gln | Tyr Glu 320 |
| Tyr | Tyr | Arg | Pro | Met 325 | Ala | Cys | Gly | Asp | Gly 330 | Gly | Tyr | Pro | Ala | Val Leu 335 |
| Asp | Glu | Ser | Ser 340 | Cys | Gln | Ser | Met | Asp 345 | Asn | Ala | Leu | Pro | Arg 350 | Cys Gln |
| Ser | Met | Ile 355 | Glu | Ser | Cys | Tyr | Ser 360 | Ser | Glu | Ser | Ala | Trp 365 | Val | Cys Val |
| Pro | Ala 370 | Ser | Ile | Tyr | Cys | Asn 375 | Asn | Ala | Leu | Leu | Ala 380 | Pro | Tyr | Gln Arg |
| Thr 385 | Gly | Gln | Asn | Val | Tyr 390 | Asp | Val | Arg | Gly | Lys 395 | Cys | Glu | Asp | Ser Ser 400 |
| Asn | Leu | Cys | Tyr | Ser 405 | Ala | Met | Gly | Tyr | Val 410 | Ser | Asp | Tyr | Leu | Asn Lys 415 |
| Pro | Glu | Val | Ile 420 | Glu | Ala | Val | Gly | Ala 425 | Glu | Val | Asn | Gly | Tyr 430 | Asp Ser |
| Cys | Asn | Phe 435 | Asp | Ile | Asn | Arg | Asn 440 | Phe | Leu | Phe | His | Gly 445 | Asp | Trp Met |
| Lys | Pro 450 | Tyr | His | Arg | Leu | Val 455 | Pro | Gly | Leu | Leu | Glu 460 | Gln | Ile | Pro Val |
| Leu 465 | Ile | Tyr | Ala | Gly | Asp 470 | Ala | Asp | Phe | Ile | Cys 475 | Asn | Trp | Leu | Gly Asn 480 |
| Lys | Ala | Trp | Thr | Glu 485 | Ala | Leu | Glu | Trp | Pro 490 | Gly | Gln | Ala | Glu | Tyr Ala 495 |
| Ser | Ala | Glu | Leu 500 | Glu | Asp | Leu | Val | Ile 505 | Val | Asp | Asn | Glu | His 510 | Thr Gly |
| Lys | Lys | Ile 515 | Gly | Gln | Val | Lys | Ser 520 | His | Gly | Asn | Phe | Thr 525 | Phe | Met Arg |
| Leu | Tyr 530 | Gly | Gly | Gly | His | Met 535 | Val | Pro | Met | Asp | Gln 540 | Pro | Glu | Ser Ser |
| Leu 545 | Glu | Phe | Phe | Asn | Arg 550 | Trp | Leu | Gly | Gly | Glu 555 | Trp | Phe | | |

( 2 ) INFORMATION FOR SEQ ID NO: 3:

( i ) SEQUENCE CHARACTERISTICS:
        ( A ) LENGTH: 2002 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Aspergillus niger ( i x ) FEATURE:
        ( A ) NAME/KEY: intron
        ( B ) LOCATION: 349..411

( i x ) FEATURE:
        ( A ) NAME/KEY: CDS
        ( B ) LOCATION: join (348..412)

( x i ) SEQUENCE DESCRIPTION: SEQ ID NO: 3:

```
GCGGCCGCTG CTACTTGCTT TTTCTAATTT GATACTTTTG TGTCCGTACC GTACCTTCCA        60

GACCGCAAGG TACCCATCCT CTACCTACTC ATCCCATCAT CATCTCGATT TCATACCAAC       120

CCCGTTGGGT TTCAACACA ATG AGA GTT CTT CCA GCT GCT ATG CTG GTT GGA       172
                      Met Arg Val Leu Pro Ala Ala Met Leu Val Gly
                       1               5                  10
```

| | | | | | | | | | | | | | | | | |
|---|---|---|---|---|---|---|---|---|---|---|---|---|---|---|---|---|
| GCG | GGC | ACT | GCG | GCC | GTC | CCT | CCC | TTC | CAG | CAG | GTC | CTT | GGA | GGT | AAC | 220 |
| Ala | Gly | Thr 15 | Ala | Ala | Val | Pro | Pro | Phe 20 | Gln | Gln | Val | Leu | Gly 25 | Gly | Asn | |
| GGT | GCC | AAG | CAC | GGT | GCC | GAC | CAT | GCG | GCC | GAG | GTC | CCT | GCG | GAT | CAC | 268 |
| Gly | Ala | Lys 30 | His | Gly | Ala | Asp | His 35 | Ala | Ala | Glu | Val | Pro 40 | Ala | Asp | His | |
| AGT | GCC | GAC | GGG | TTC | TCC | AAG | CCG | CTG | CAC | GCA | TTC | CAG | GAG | GAG | CTG | 316 |
| Ser | Ala 45 | Asp | Gly | Phe | Ser 50 | Lys | Pro | Leu | His | Ala 55 | Phe | Gln | Glu | Glu | Leu | |
| AAG | TCT | CTC | TCT | GAT | GAG | GCT | CGT | AAG | CTC | TGG | GAT | GAG | GTT | GCT | AGC | 364 |
| Lys 60 | Ser | Leu | Ser | Asp | Glu 65 | Ala | Arg | Lys | Leu | Trp 70 | Asp | Glu | Val | Ala | Ser 75 | |
| TTC | TTC | CCG | GAG | AGC | ATG | GAT | CAG | AAC | CCT | CTC | TTC | TCC | CTC | CCC | AAG | 412 |
| Phe | Phe | Pro | Glu | Ser 80 | Met | Asp | Gln | Asn | Pro 85 | Leu | Phe | Ser | Leu | Pro 90 | Lys | |
| AAG | CAC | AAC | CGC | CGC | CCC | GAC | CAC | CAC | TGG | GAC | CAC | ATC | GTC | CGC | GGC | 460 |
| Lys | His | Asn | Arg 95 | Arg | Pro | Asp | His | His 100 | Trp | Asp | His | Ile | Val 105 | Arg | Gly | |
| TCC | GAC | GTT | CAG | AGC | GTC | TGG | GTT | ACT | GGT | GAG | AAC | GGT | GAG | AAG | GAG | 508 |
| Ser | Asp | Val 110 | Gln | Ser | Val | Trp | Val 115 | Thr | Gly | Glu | Asn | Gly 120 | Glu | Lys | Glu | |
| CGT | GAG | GTC | GAT | GGC | AAG | CTG | GAA | GCC | TAT | GAT | CTC | AGG | GTC | AAG | AAG | 556 |
| Arg | Glu 125 | Val | Asp | Gly | Lys 130 | Leu | Glu | Ala | Tyr | Asp 135 | Leu | Arg | Val | Lys | Lys | |
| ACC | GAT | CCT | AGC | TCT | CTT | GGC | ATC | GAC | CCT | GGC | GTA | AAG | CAG | TAC | ACC | 604 |
| Thr 140 | Asp | Pro | Ser | Ser | Leu 145 | Gly | Ile | Asp | Pro | Gly 150 | Val | Lys | Gln | Tyr | Thr 155 | |
| GGT | TAT | CTC | GAT | GAC | AAC | GAG | AAC | GAC | AAG | CAT | CTG | TTC | TAC | TGG | TTC | 652 |
| Gly | Tyr | Leu | Asp | Asp 160 | Asn | Glu | Asn | Asp | Lys 165 | His | Leu | Phe | Tyr | Trp 170 | Phe | |
| TTC | GAG | TCT | CGC | AAT | GAC | CCC | GAG | AAT | GAC | CCT | GTT | GTT | CTG | TGG | CTG | 700 |
| Phe | Glu | Ser | Arg 175 | Asn | Asp | Pro | Glu | Asn 180 | Asp | Pro | Val | Val | Leu 185 | Trp | Leu | |
| AAC | GGT | GGC | CCT | GGA | TGC | TCT | TCC | CTC | ACC | GGT | CTT | TTC | ATG | GAG | CTC | 748 |
| Asn | Gly | Gly 190 | Pro | Gly | Cys | Ser | Ser 195 | Leu | Thr | Gly | Leu | Phe 200 | Met | Glu | Leu | |
| GGC | CCT | AGC | AGC | ATC | AAC | AAG | AAG | ATC | CAG | CCG | GTC | TAC | AAC | GAC | TAC | 796 |
| Gly | Pro 205 | Ser | Ser | Ile | Asn 210 | Lys | Lys | Ile | Gln | Pro 215 | Val | Tyr | Asn | Asp | Tyr | |
| GCT | TGG | AAC | TCC | AAC | GCG | TCC | GTG | ATC | TTC | CTT | GAC | CAG | CCT | GTC | AAC | 844 |
| Ala 220 | Trp | Asn | Ser | Asn | Ala 225 | Ser | Val | Ile | Phe | Leu 230 | Asp | Gln | Pro | Val | Asn 235 | |
| GTC | GGT | TAC | TCT | TAC | AGC | AAC | TCT | GCT | GTC | AGC | GAC | ACC | GTT | GCT | GCT | 892 |
| Val | Gly | Tyr | Ser | Tyr 240 | Ser | Asn | Ser | Ala | Val 245 | Ser | Asp | Thr | Val | Ala 250 | Ala | |
| GGC | AAG | GAC | GTC | TAT | GCC | TTG | CTT | ACC | CTC | TTC | TTC | AAA | CAA | TTC | CCC | 940 |
| Gly | Lys | Asp | Val 255 | Tyr | Ala | Leu | Leu | Thr 260 | Leu | Phe | Phe | Lys | Gln 265 | Phe | Pro | |
| GAG | TAT | GCC | AAG | CAG | GAC | TTC | CAC | ATT | GCC | GGT | GAA | TCC | TAT | GCT | GGT | 988 |
| Glu | Tyr | Ala | Lys 270 | Gln | Asp | Phe | His 275 | Ile | Ala | Gly | Glu | Ser 280 | Tyr | Ala | Gly | |
| CAC | TAT | ATC | CCC | GTC | TTT | GCT | TCG | GAG | ATT | TTG | TCT | CAC | AAG | AAG | CGC | 1036 |
| His | Tyr 285 | Ile | Pro | Val | Phe | Ala 290 | Ser | Glu | Ile | Leu | Ser 295 | His | Lys | Lys | Arg | |
| AAC | ATC | AAC | CTG | CAG | TCC | GTT | CTT | ATT | GGC | AAC | GGT | CTC | ACC | GAC | GGT | 1084 |
| Asn | Ile | Asn | Leu 300 | Gln | Ser | Val | Leu | Ile 305 | Gly | Asn | Gly | Leu | Thr 310 | Asp | Gly 315 | |
| CTC | ACT | CAG | TAC | GAG | TAC | TAC | CGT | CCC | ATG | GCC | TGT | GGT | GAC | GGT | GGT | 1132 |
| Leu | Thr | Gln | Tyr | Glu 320 | Tyr | Tyr | Arg | Pro | Met 325 | Ala | Cys | Gly | Asp | Gly 330 | Gly | |

| | | | | | | | | | | | | | | | | |
|---|---|---|---|---|---|---|---|---|---|---|---|---|---|---|---|---|
| TAC | CCA | GCT | GTC | TTG | GAC | GAG | GGC | TCC | TGC | CAG | GCC | ATG | GAC | AAC | GCC | 1180 |
| Tyr | Pro | Ala | Val | Leu | Asp | Glu | Gly | Ser | Cys | Gln | Ala | Met | Asp | Asn | Ala | |
| | | | 335 | | | | 340 | | | | | 345 | | | | |
| CTT | CCT | CGC | TGC | CAG | TCT | ATG | ATT | GAG | TCT | TGC | TAT | AGT | TCC | GAG | AGC | 1228 |
| Leu | Pro | Arg | Cys | Gln | Ser | Met | Ile | Glu | Ser | Cys | Tyr | Ser | Ser | Glu | Ser | |
| | | 350 | | | | | 355 | | | | | 360 | | | | |
| GCT | TGG | GTT | TGT | GTC | CCG | GCC | TCC | ATC | TAC | TGT | AAC | AAC | GCC | CTC | CTT | 1276 |
| Ala | Trp | Val | Cys | Val | Pro | Ala | Ser | Ile | Tyr | Cys | Asn | Asn | Ala | Leu | Leu | |
| | 365 | | | | | 370 | | | | | 375 | | | | | |
| GCC | CCT | TAC | CAG | CGC | ACC | GGA | CAG | AAC | GTC | TAC | GAT | GTT | CGT | GGT | AAG | 1324 |
| Ala | Pro | Tyr | Gln | Arg | Thr | Gly | Gln | Asn | Val | Tyr | Asp | Val | Arg | Gly | Lys | |
| 380 | | | | | 385 | | | | | 390 | | | | | 395 | |
| TGC | GAG | GAT | AGC | TCC | AAC | CTC | TGC | TAC | TCG | GCC | ATG | GGC | TAC | GTC | AGC | 1372 |
| Cys | Glu | Asp | Ser | Ser | Asn | Leu | Cys | Tyr | Ser | Ala | Met | Gly | Tyr | Val | Ser | |
| | | | | 400 | | | | | 405 | | | | | 410 | | |
| GAC | TAC | CTG | AAC | AAG | ACC | GAG | GTC | ATT | GAG | GCT | GTT | GGC | GCT | GAG | GTC | 1420 |
| Asp | Tyr | Leu | Asn | Lys | Thr | Glu | Val | Ile | Glu | Ala | Val | Gly | Ala | Glu | Val | |
| | | | 415 | | | | | 420 | | | | | 425 | | | |
| AAC | GGC | TAC | GAC | TCG | TGC | AAC | TTT | GAC | ATC | AAC | CGC | AAC | TTC | CTC | TTC | 1468 |
| Asn | Gly | Tyr | Asp | Ser | Cys | Asn | Phe | Asp | Ile | Asn | Arg | Asn | Phe | Leu | Phe | |
| | | 430 | | | | | 435 | | | | | 440 | | | | |
| CAC | GGT | GAC | TGG | ATG | AAG | CCC | TAC | CAC | CGT | CTC | GTT | CCG | GGA | CTC | CTG | 1516 |
| His | Gly | Asp | Trp | Met | Lys | Pro | Tyr | His | Arg | Leu | Val | Pro | Gly | Leu | Leu | |
| | 445 | | | | | 450 | | | | | 455 | | | | | |
| GAG | CAG | ATC | CCT | GTC | CTG | ATC | TAC | GCT | GGT | GAC | GCC | GAT | TTC | ATC | TGC | 1564 |
| Glu | Gln | Ile | Pro | Val | Leu | Ile | Tyr | Ala | Gly | Asp | Ala | Asp | Phe | Ile | Cys | |
| 460 | | | | | 465 | | | | | 470 | | | | | 475 | |
| AAC | TGG | CTG | GGC | AAC | AAG | GCC | TGG | ACT | GAA | GCC | CTT | GAG | TGG | CCC | GGA | 1612 |
| Asn | Trp | Leu | Gly | Asn | Lys | Ala | Trp | Thr | Glu | Ala | Leu | Glu | Trp | Pro | Gly | |
| | | | | 480 | | | | | 485 | | | | | 490 | | |
| CAG | GCT | GAA | TAT | GCC | TCC | GCT | AAG | CTG | GAG | GAC | CTG | GTC | GTG | GTC | GAG | 1660 |
| Gln | Ala | Glu | Tyr | Ala | Ser | Ala | Lys | Leu | Glu | Asp | Leu | Val | Val | Val | Glu | |
| | | | 495 | | | | | 500 | | | | | 505 | | | |
| AAT | GAG | CAC | AAG | GGC | AAG | AAG | ATC | GGC | CAG | GTC | AAG | TCC | CAT | GGC | AAC | 1708 |
| Asn | Glu | His | Lys | Gly | Lys | Lys | Ile | Gly | Gln | Val | Lys | Ser | His | Gly | Asn | |
| | | 510 | | | | | 515 | | | | | 520 | | | | |
| TTC | ACC | TTC | ATG | CGT | CTC | TAT | GGC | GGT | GGC | CAC | ATG | GTC | CCG | ATG | GAC | 1756 |
| Phe | Thr | Phe | Met | Arg | Leu | Tyr | Gly | Gly | Gly | His | Met | Val | Pro | Met | Asp | |
| | 525 | | | | | 530 | | | | | 535 | | | | | |
| CAA | CCC | GAG | TCG | AGT | CTT | GAA | TTC | TTC | AAC | CGC | TGG | TTG | GGA | GGT | GAA | 1804 |
| Gln | Pro | Glu | Ser | Ser | Leu | Glu | Phe | Phe | Asn | Arg | Trp | Leu | Gly | Gly | Glu | |
| 540 | | | | | 545 | | | | | 550 | | | | | 555 | |
| TGG | TTT | TAA | AGACGTGCTA | TCACCGCATA | TAGACTTTCC | GGTCATTTCG | GTGACACTGC | | | | | | | | | 1863 |
| Trp | Phe | | | | | | | | | | | | | | | |

AGATATGTTT CTTAACGATA GTTTGAGGAT GCTTGTCAAT GCCCACTAAT CCCGAGCCTT 1923

ATGTTACATG GTATCTATGA GTTTGTCATT ATAGTGCATT ATGCATTTGT ACTCCGTACG 1983

AGAATGAATC AGCGGCCGC 2002

( 2 ) INFORMATION FOR SEQ ID NO: 4:

( i ) SEQUENCE CHARACTERISTICS:
        ( A ) LENGTH: 557 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Aspergillus Niger ( x i ) SEQUENCE DESCRIPTION: SEQ ID NO: 4:

| | | | | | | | | | | | | | | |
|---|---|---|---|---|---|---|---|---|---|---|---|---|---|---|
| Met | Arg | Val | Leu | Pro | Ala | Ala | Met | Leu | Val | Gly | Ala | Gly | Thr | Ala | Ala |
| 1 | | | | 5 | | | | | 10 | | | | | 15 | |
| Val | Pro | Pro | Phe | Gln | Gln | Val | Leu | Gly | Gly | Asn | Gly | Ala | Lys | His | Gly |
| | | | 20 | | | | | 25 | | | | | 30 | | |
| Ala | Asp | His | Ala | Ala | Glu | Val | Pro | Ala | Asp | His | Ser | Ala | Asp | Gly | Phe |
| | | 35 | | | | | 40 | | | | | 45 | | | |
| Ser | Lys | Pro | Leu | His | Ala | Phe | Gln | Glu | Glu | Leu | Lys | Ser | Leu | Ser | Asp |
| | 50 | | | | | 55 | | | | | 60 | | | | |
| Glu | Ala | Arg | Lys | Leu | Trp | Asp | Glu | Val | Ala | Ser | Phe | Phe | Pro | Glu | Ser |
| 65 | | | | | 70 | | | | | 75 | | | | | 80 |
| Met | Asp | Gln | Asn | Pro | Leu | Phe | Ser | Leu | Pro | Lys | Lys | His | Asn | Arg | Arg |
| | | | | 85 | | | | | 90 | | | | | 95 | |
| Pro | Asp | His | His | Trp | Asp | His | Ile | Val | Arg | Gly | Ser | Asp | Val | Gln | Ser |
| | | | 100 | | | | | 105 | | | | | 110 | | |
| Val | Trp | Val | Thr | Gly | Glu | Asn | Gly | Glu | Lys | Glu | Arg | Glu | Val | Asp | Gly |
| | | | 115 | | | | | 120 | | | | | 125 | | |
| Lys | Leu | Glu | Ala | Tyr | Asp | Leu | Arg | Val | Lys | Lys | Thr | Asp | Pro | Ser | Ser |
| | | 130 | | | | | 135 | | | | | 140 | | | |
| Leu | Gly | Ile | Asp | Pro | Gly | Val | Lys | Gln | Tyr | Thr | Gly | Tyr | Leu | Asp | Asp |
| 145 | | | | | 150 | | | | | 155 | | | | | 160 |
| Asn | Glu | Asn | Asp | Lys | His | Leu | Phe | Tyr | Trp | Phe | Phe | Glu | Ser | Arg | Asn |
| | | | | 165 | | | | | 170 | | | | | 175 | |
| Asp | Pro | Glu | Asn | Asp | Pro | Val | Val | Leu | Trp | Leu | Asn | Gly | Gly | Pro | Gly |
| | | | | 180 | | | | | 185 | | | | | 190 | |
| Cys | Ser | Ser | Leu | Thr | Gly | Leu | Phe | Met | Glu | Leu | Gly | Pro | Ser | Ser | Ile |
| | | 195 | | | | | 200 | | | | | 205 | | | |
| Asn | Lys | Lys | Ile | Gln | Pro | Val | Tyr | Asn | Asp | Tyr | Ala | Trp | Asn | Ser | Asn |
| | 210 | | | | | 215 | | | | | 220 | | | | |
| Ala | Ser | Val | Ile | Phe | Leu | Asp | Gln | Pro | Val | Asn | Val | Gly | Tyr | Ser | Tyr |
| 225 | | | | | 230 | | | | | 235 | | | | | 240 |
| Ser | Asn | Ser | Ala | Val | Ser | Asp | Thr | Val | Ala | Ala | Gly | Lys | Asp | Val | Tyr |
| | | | | 245 | | | | | 250 | | | | | 255 | |
| Ala | Leu | Leu | Thr | Leu | Phe | Phe | Lys | Gln | Phe | Pro | Glu | Tyr | Ala | Lys | Gln |
| | | | 260 | | | | | 265 | | | | | 270 | | |
| Asp | Phe | His | Ile | Ala | Gly | Glu | Ser | Tyr | Ala | Gly | His | Tyr | Ile | Pro | Val |
| | | 275 | | | | | 280 | | | | | 285 | | | |
| Phe | Ala | Ser | Glu | Ile | Leu | Ser | His | Lys | Lys | Arg | Asn | Ile | Asn | Leu | Gln |
| | 290 | | | | | 295 | | | | | 300 | | | | |
| Ser | Val | Leu | Ile | Gly | Asn | Gly | Leu | Thr | Asp | Gly | Leu | Thr | Gln | Tyr | Glu |
| 305 | | | | | 310 | | | | | 315 | | | | | 320 |
| Tyr | Tyr | Arg | Pro | Met | Ala | Cys | Gly | Asp | Gly | Gly | Tyr | Pro | Ala | Val | Leu |
| | | | | 325 | | | | | 330 | | | | | 335 | |
| Asp | Glu | Gly | Ser | Cys | Gln | Ala | Met | Asp | Asn | Ala | Leu | Pro | Arg | Cys | Gln |
| | | | 340 | | | | | 345 | | | | | 350 | | |
| Ser | Met | Ile | Glu | Ser | Cys | Tyr | Ser | Ser | Glu | Ser | Ala | Trp | Val | Cys | Val |
| | | 355 | | | | | 360 | | | | | 365 | | | |
| Pro | Ala | Ser | Ile | Tyr | Cys | Asn | Asn | Ala | Leu | Leu | Ala | Pro | Tyr | Gln | Arg |
| | 370 | | | | | 375 | | | | | 380 | | | | |
| Thr | Gly | Gln | Asn | Val | Tyr | Asp | Val | Arg | Gly | Lys | Cys | Glu | Asp | Ser | Ser |
| 385 | | | | | 390 | | | | | 395 | | | | | 400 |
| Asn | Leu | Cys | Tyr | Ser | Ala | Met | Gly | Tyr | Val | Ser | Asp | Tyr | Leu | Asn | Lys |
| | | | | 405 | | | | | 410 | | | | | 415 | |
| Thr | Glu | Val | Ile | Glu | Ala | Val | Gly | Ala | Glu | Val | Asn | Gly | Tyr | Asp | Ser |

-continued

|     |     |     | 420 |     |     |     | 425 |     |     |     | 430 |     |     |     |
|-----|-----|-----|-----|-----|-----|-----|-----|-----|-----|-----|-----|-----|-----|-----|
| Cys | Asn | Phe 435 | Asp | Ile | Asn | Arg | Asn 440 | Phe | Leu | Phe | His | Gly 445 | Asp | Trp | Met |
| Lys | Pro 450 | Tyr | His | Arg | Leu | Val 455 | Pro | Gly | Leu | Leu | Glu 460 | Gln | Ile | Pro | Val |
| Leu 465 | Ile | Tyr | Ala | Gly | Asp 470 | Ala | Asp | Phe | Ile | Cys 475 | Asn | Trp | Leu | Gly | Asn 480 |
| Lys | Ala | Trp | Thr | Glu 485 | Ala | Leu | Glu | Trp | Pro 490 | Gly | Gln | Ala | Glu | Tyr 495 | Ala |
| Ser | Ala | Lys | Leu 500 | Glu | Asp | Leu | Val | Val 505 | Val | Glu | Asn | Glu | His 510 | Lys | Gly |
| Lys | Lys | Ile 515 | Gly | Gln | Val | Lys | Ser 520 | His | Gly | Asn | Phe | Thr 525 | Phe | Met | Arg |
| Leu | Tyr 530 | Gly | Gly | Gly | His | Met 535 | Val | Pro | Met | Asp | Gln 540 | Pro | Glu | Ser | Ser |
| Leu 545 | Glu | Phe | Phe | Asn | Arg 550 | Trp | Leu | Gly | Gly | Glu 555 | Trp | Phe |